United States Patent
Osgood et al.

(10) Patent No.: US 10,049,865 B2
(45) Date of Patent: Aug. 14, 2018

(54) INTELLIGENTLY CONTROLLED SPECTROMETER METHODS AND APPARATUS

(71) Applicants: Mark A Osgood, Brookline, NH (US); Ching Wu, Boxborough, MA (US)

(72) Inventors: Mark A Osgood, Brookline, NH (US); Ching Wu, Boxborough, MA (US)

(73) Assignee: Excellims Corporation, Acton, MA (US)

(*) Notice: Subject to any disclaimer, the term of this patent is extended or adjusted under 35 U.S.C. 154(b) by 46 days.

(21) Appl. No.: 14/703,868

(22) Filed: May 4, 2015

(65) Prior Publication Data
US 2015/0303043 A1    Oct. 22, 2015

Related U.S. Application Data

(63) Continuation of application No. 12/764,808, filed on Apr. 21, 2010, now Pat. No. 9,024,255, and a continuation-in-part of application No. 11/776,392, filed on Jul. 11, 2007, now abandoned.

(60) Provisional application No. 61/171,447, filed on Apr. 21, 2009.

(51) Int. Cl.
| | |
|---|---|
| H01J 49/00 | (2006.01) |
| C07B 63/00 | (2006.01) |
| G01N 27/62 | (2006.01) |
| H01J 49/04 | (2006.01) |
| H01J 49/06 | (2006.01) |

(52) U.S. Cl.
CPC ............ *H01J 49/004* (2013.01); *C07B 63/00* (2013.01); *G01N 27/622* (2013.01); *H01J 49/0027* (2013.01); *H01J 49/0031* (2013.01); *H01J 49/0495* (2013.01); *H01J 49/067* (2013.01)

(58) Field of Classification Search
None
See application file for complete search history.

(56) References Cited

U.S. PATENT DOCUMENTS

| | | | | |
|---|---|---|---|---|
| RE33,863 E | * | 3/1992 | Bowman | F16K 31/007 250/288 |
| 5,092,155 A | * | 3/1992 | Rounbehler | G01N 1/02 436/156 |
| 5,092,156 A | * | 3/1992 | Miskolczy | G01N 1/02 436/156 |
| 5,092,157 A | * | 3/1992 | Achter | G01N 1/02 436/156 |
| 5,092,217 A | * | 3/1992 | Achter | G01N 1/02 73/1.04 |

(Continued)

FOREIGN PATENT DOCUMENTS

| | | | | |
|---|---|---|---|---|
| GB | 2413433 A | * | 10/2005 | G01N 27/624 |
| GB | 2413433 B | * | 3/2007 | G01N 27/624 |

*Primary Examiner* — Andrew Smyth

(57) ABSTRACT

The present invention relates to improving the ability of a hyphenated instrument to analyze a sample benefiting from having the first instrument's analysis of the same sample. A fast switching mechanism can be used as the interface between an ion mobility spectrometer (IMS) and a mass spectrometer (MS) such that the obtained IMS spectrum is converted into a timing diagram that controls the vacuum inlet's size dynamically during analysis of a neutral and/or charged chemical and/or biological species such that a smaller pumping system can be used.

12 Claims, 6 Drawing Sheets

(56) References Cited

U.S. PATENT DOCUMENTS

| | | | | |
|---|---|---|---|---|
| 5,092,219 A | * | 3/1992 | Rounbehler | G01N 1/02 102/301 |
| 5,092,220 A | * | 3/1992 | Rounbehler | G01N 33/0037 89/1.1 |
| 5,099,743 A | * | 3/1992 | Rounbehler | G01N 1/02 436/156 |
| 5,123,274 A | * | 6/1992 | Carroll | G01N 1/02 436/156 |
| 5,310,681 A | * | 5/1994 | Rounbehler | G01N 1/02 436/106 |
| 5,420,425 A | * | 5/1995 | Bier | H01J 49/423 250/282 |
| 5,485,016 A | * | 1/1996 | Irie | H01J 49/0422 250/281 |
| 5,572,022 A | * | 11/1996 | Schwartz | H01J 49/147 250/282 |
| 5,710,427 A | * | 1/1998 | Schubert | H01J 49/424 250/282 |
| 5,969,350 A | * | 10/1999 | Kerley | H01J 49/164 250/287 |
| 6,323,482 B1 | * | 11/2001 | Clemmer | G01N 27/622 250/282 |
| 6,744,043 B2 | * | 6/2004 | Loboda | G01N 27/622 250/282 |
| 6,744,046 B2 | * | 6/2004 | Valaskovic | H01J 49/165 239/3 |
| 6,784,439 B2 | * | 8/2004 | Van Berkel | H01J 49/04 250/281 |
| 6,987,264 B1 | * | 1/2006 | Whitehouse | H01J 49/004 250/292 |
| 6,992,283 B2 | * | 1/2006 | Bateman | G01N 27/622 250/281 |
| 7,057,168 B2 | * | 6/2006 | Miller | G01N 27/622 250/281 |
| 7,112,453 B2 | * | 9/2006 | Hutchens | B01J 20/281 436/525 |
| 7,122,794 B1 | * | 10/2006 | Miller | H01J 49/0013 250/294 |
| 7,230,234 B2 | * | 6/2007 | Kobayashi | H01J 49/0495 250/281 |
| 7,232,109 B2 | * | 6/2007 | Driggs | F15C 5/00 251/129.01 |
| 7,241,989 B2 | * | 7/2007 | Miller | G01N 27/622 250/281 |
| 2002/0190203 A1 | * | 12/2002 | Valaskovic | H01J 49/165 250/288 |
| 2004/0094702 A1 | * | 5/2004 | Clemmer | G01N 27/622 250/283 |
| 2004/0173743 A1 | * | 9/2004 | Valaskovic | H01J 49/165 250/288 |
| 2005/0051719 A1 | * | 3/2005 | Miller | G01N 27/622 250/287 |
| 2005/0127289 A1 | * | 6/2005 | Fuhrer | H01J 49/025 250/288 |
| 2005/0230615 A1 | * | 10/2005 | Furutani | B82Y 10/00 250/287 |
| 2005/0242279 A1 | * | 11/2005 | Verentchikov | H01J 49/004 250/287 |
| 2006/0151687 A1 | * | 7/2006 | Miller | G01N 27/622 250/282 |
| 2006/0249671 A1 | * | 11/2006 | Karpetsky | G01N 27/624 250/288 |
| 2010/0001182 A1 | * | 1/2010 | Burchfield | G01N 27/624 250/283 |

* cited by examiner

INTELLIGENTLY CONTROLLED SPECTROMETER METHODS AND APPARATUS

CROSS-REFERENCE TO RELATED APPLICATIONS

The present application is a continuation of U.S. patent application Ser. No. 12/764,808, filed on Apr. 21, 2010, which is a continuation in part of U.S. patent application Ser. No. 11/776,392, filed on Jul. 11, 2007, and claims the benefit of and priority to corresponding U.S. Provisional Patent Application No. 61/171,447, filed Apr. 21, 2009 respectively; the entire content of these cross-referenced applications is herein incorporated by reference.

BACKGROUND OF THE INVENTION

Most analytical instruments have been developed to be used as individual units for analysis of a sample. Some of these individual units have been combined to give more information from a single sample run. These combined individual units still work as separate analysis tools in that a full run or spectrum is taken for each unit, but the first unit can transfer separated components of the sample to the next unit. Effectively using multiple analytical instruments as a hyphenated instrument allows analysis of a sample based on multiple analytical principles with limited sample usage and instrument run time.

The present invention relates to improving the ability of a hyphenated instrument to analyze a sample benefiting from having the first instrument's analysis of the same sample. For example, a fast switching mechanism can be used as the interface between an ion mobility spectrometer (IMS) and a mass spectrometer (MS) such that the IMS spectrum obtained outside the vacuum chamber is converted into a timing diagram that controls the vacuum inlet's size dynamically during analysis of a neutral and/or charged chemical and/or biological species so that a smaller pumping system can be used.

SUMMARY OF THE INVENTION

A device and/or program that may be used to control a vacuum inlet's size dynamically during analysis of a neutral and/or charged chemical and/or biological species. With a dynamically controlled vacuum inlet, only a smaller amount of gas would be needed to be pumped for the analysis to be conducted in the vacuum chamber; an ion mobility spectrometer—mass spectrometer (IMS-MS) instrument can be constructed in a compact form when using a dynamically controlling the vacuum inlet. As a non-limiting example, a portable ion mobility spectrometer—mass spectrometer (IMS-MS) instrument can be constructed in a compact form when using a dynamically controlled vacuum inlet for the MS.

The simplified example of this device is shown below in Scheme 1. In various embodiments, a signal detector outside the vacuum chamber can be used to detect the arrival of the sample of interest, and then use the detected signal to generate programs to control the vacuum inlet. In one embodiment, the program(s) is used to control the timing for opening and closing valves at the vacuum inlet. Scheme 2 below shows a non-limiting example where the open valve timing is controlled using the arrival peak timing in an IMS spectrum.

Not only the signal from an IMS, the valve timing can be controlled by running other analytical and preparative separation methods (in the gas or liquid phase) for given sample(s) prior to the analysis in the vacuum system, such as mass analysis. Many known instrumental methods can be used to obtain sample arrival information and control the vacuum valve timing for mass analysis, such instruments may include, but not limited to, IMS with Faraday plate detector, gas chromatography (GC) with a FID detector, liquid chromatograph (LC) and/or electrophoresis with a UV detector, and a variety of separation and/or detection methods and their combination that could used before entering the vacuum chamber.

BRIEF DESCRIPTION OF THE DRAWINGS

The foregoing and other aspects, embodiments, and features of the inventions can be more fully understood from the following description in conjunction with the accompanying drawings. In the drawings like reference characters generally refer to like features and structural elements throughout the various figures. The drawings are not necessarily to scale, emphasis instead being placed upon illustrating the principles of the inventions.

DETAILED DESCRIPTION OF VARIOUS EMBODIMENTS

Figure 1:
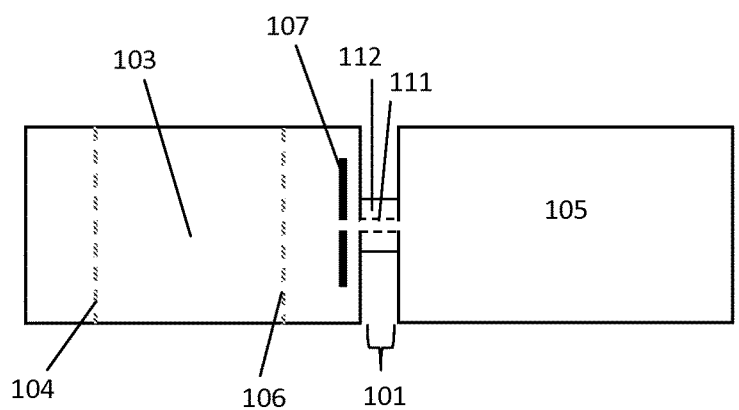
FIG. 1 shows a fast switching valve as the interface between an IMS and a MS.

The piezoelectric (or other suitable material) valve/interface can be used to control the amount of ions entering a mass spectrometer. The valve/interface open/close timing can be controlled such that the valve/interface is open only when ions are passing through the valve/interface instead of being constantly open. The open valve timing can be controlled by running a spectrum of the sample prior to mass analysis, such as an IMS spectrum, but not limited to this instrument. Any known instrument can be used to control the open valve timing for mass analysis, such as: GC, IMS, LC, CE, etc, but not limited to only these. Current mass spectrometer systems have the valve/interface constantly open. This invention reduces the vacuum pumping requirement for the mass spectrometer. For example, if the vacuum system is open to the atmospheric pressure for 20% of the time, then the vacuum pump may only need to handle ⅕ of the load, therefore the pumping system can be much smaller. This method is particularly meaningful for portable mass spectrometer applications.

The term ion mobility separator, and ion mobility spectrometer, and ion mobility based spectrometers are used interchangeably in this invention, often referred to as IMS, including time-of-flight (TOF) IMS, differential mobility spectrometers (DMS), field asymmetric ion mobility spectrometers (FAIMS) and their derived forms. A time of flight ion mobility spectrometer and their derived forms refers to, in its broadest sense, any ion mobility based separation device that characterize ions based on their time of flight over a defined distance. A FAIMS, a DMS, and their derived forms separate ions based on their ion mobility characteristics under high values of normalized electric field. The IMS systems may operate in different drift media, such as gas and/or liquid, in their pure or mixture forms. The operating pressure may vary from low vacuum to a plurality of atmospheric pressures.

The systems and methods of the present inventions may make use of "drift tubes." The term "drift tube" is used herein in accordance with the accepted meaning of that term in the field of ion mobility spectrometry. A drift tube is a structure containing a neutral gas through which ions are moved under the influence of an electrical field. It is to be understood that a "drift tube" does not need to be in the form of a tube or cylinder. As understood in the art, a "drift tube" is not limited to the circular or elliptical cross-sections found in a cylinder, but can have any cross-sectional shape including, but not limited to, square, rectangular, circular, elliptical, semi-circular, triangular, etc. In many cases, a drift tube is also referred to the ion transportation and/or ion filter section of a FAIMS or DMS device.

Neutral gas is often referred to as a carrier gas, drift gas, buffer gas, etc. and these terms are considered interchangeable herein. The gas is at a pressure such that the mean free path of the ion, or ions, of interest is less than the dimensions of the drift tube. That is the gas pressure is chosen for viscous flow. Under conditions of viscous flow of a gas in a channel, conditions are such that the mean free path is very small compared with the transverse dimensions of the channel. At these pressures the flow characteristics are determined mainly by collisions between the gas molecules, i.e. the viscosity of the gas. The flow may be laminar or turbulent. It is preferred that the pressure in the drift tube is high enough that ions will travel a negligible distance, relative to the longitudinal length of the drift tube, therefore a steady-state ion mobility is achieved. An IMS can be used at different pressure conditions.

The present invention describes generating a timing program using a first method; using the timing program to intelligently control the open-close action of a vacuum inlet; analyzing a sample using a second method under vacuum conditions. The present invention also describes the apparatus being designed to realize these novel methods. The invention allows conducting analysis of the sample of interest under vacuum conditions with a reduced pumping capacity. Enabling construction of a compact/portable analytical instrument that requires vacuum operating conditions, such as a mass spectrometer; furthermore, a portable IMS-MS instrument is desirable.

Timing can be generated based on a theoretical calculation of known samples, for example, the explosives of interest have certain ion mobility, Ko, therefore the drift time of these samples in a IMS under the given conditions are known. The vacuum inlet can be programmed to open when these peaks arrive after the IMS analysis.

In various embodiments of the above mentioned method and apparatus, a known instrument and/or program can be used to open and close the vacuum inlet according to a predetermined timing program. One embodiment is to use a survey scan and/or pre-run to determine the arrival time of the sample for the analysis under vacuum conditions. For example, an IMS spectrum can be obtained prior to the analysis under vacuum conditions, generating the timing program based on the drift times of the analytes in IMS spectrum, which only open the vacuum inlet when the analytes arrive at the inlet. Similarly, the timing program can be generated using other instruments such as: GC, LC, CE, etc, but not limited to only these, to control the inlet to a vacuum. In alternative embodiments, the timing program used to control the vacuum inlet could be predetermined based on prior knowledge of an instrument. For example, if the retention time for Protein A and Protein B are known to be 4 and 6 minutes, respectively, under giving chromatographic conditions, and then the timing program is set to open at the $4^{th}$ and $6^{th}$ minute with a width of for instance 30 second, depending on the resolution of the chromatographic system.

Not only controlling the vacuum inlet, the timing program can also be used to set the operational parameters for the mass spectrometer. For example, when a quadrupole mass spectrometer is used, a table of m/z values and/or ranges that are predicted according to the ion mobility and/or chromatographic data obtained using the first method could be preload to the mass spectrometer. Rapid and/or selective mass measurement using a quadrupole mass spectrometer could be achieved. For example, when an orthogonal TOF mass spectrometer is used, preferred orthogonal extraction timing could be selected to maximize the sensitivity of compounds to be measured using the TOF mass spectrometer. In one embodiment, an ion mobility measurement is used as the first method to generate the timing program and then setting the optimal mass spectrometer operational parameters according to ion mobility peak identified on IMS; note that the IMS device could be operated either ambient or low/high pressure conditions. The timing program used to control a mass spectrometer could be generated either on-the-fly or previous to mass measurement offline.

A preferred embodiment for this invention is to control the vacuum inlet open-close timing "on-the-fly". The dynamic control is realized by using a first instrument to detect arrival of the sample, opening the vacuum inlet while the sample arrives at the inlet, closing the inlet after allowing some of the sample into the inlet; the opening and closing process may repeat during the course of operating the system in order to allow all sample of interest enters the vacuum with the reduced size vacuum system. For example, using a LC with a UV detector hyphenated with a MS, during the LC-MS operation, the UV detector can first detect the arrival of Protein A at the end of the LC column, and then send a control signal to the intelligent vacuum inlet control module to open the inlet for Protein A, as Protein A will take 'X' amount of time to be transported from the UV detector to the vacuum inlet via pumping the mobile phase; the vacuum inlet will open after 'X' delay.

In one embodiment of the on-the-fly control for the vacuum inlet (or the mass spectrometer operational parameters), the ion detector of the IMS that is in front of the mass spectrometer can be positioned at a location that is away from the vacuum inlet. At the ion detector at least some of the ions are detected and the rest of the ions continuously traveling toward the vacuum inlet of the mass spectrometer. The position of the detector may be selected to give sufficient time for programming the vacuum inlet or the mass spectrometer. For example, if the ion detector locates at 2 cm from the vacuum inlet, under an electric field condition of 300 V/cm, for ions with mobility of 2.5 $cm^2$/Vs, it will take 2.7 ms for these ions to reach the vacuum inlet and this amount of time can be used to program the vacuum inlet or the mass spectrometer. Consideration will be given to maintain the resolution of the mobility separated ions while transporting the ions (using electric field, air flow, and/or other means) from the IMS detector to the mass spectrometer. The IMS detector can be any means to detect a portion of the ions. A common IMS detector can be a Faraday plate. The detector can be made in a shape of ring, bar, or any other geometries where the ion beam aiming at the vacuum inlet is not interfered.

In a variety of the IMS-MS embodiments, a quadrupole mass spectrometer could be implemented by linking the mass scan functions with the timing program of the ion mobility based separation. A non-limiting example is to track the DC and RF voltages that are used for the mass scan with the timing program according to the mass-mobility correlation. In this case, once a peak is detected on the ion mobility detector in front of the mass analyzer (either outside or inside the vacuum chamber), the DC and RF voltage (that determines the m/z of the ions that can pass through the analyzer) will not need to change over a large range of voltage changes (especially for the RF voltage), thus it minimizes the settling time required for setting the mass analyzer to identify targeted compounds. In this operation, the mass analyzer may "park" on one or more m/z value for a short period for mass measurement, and then resume tracking the timing program. Tracking the mass analyzer setting with the time program generated by the IMS will also prepare the MS to be ready to scan a mass range correlated from the timing program.

In addition, the load of a vacuum system needs to be controlled in a manner where the desired vacuum conditions can be maintained. Even though it is ideal to control the vacuum inlet completely according to arrival time of the sample, additional approaches need to be considered when the inlet opening time is significant (it will overload a given vacuum system). These approaches may include, but are not limited to: (1) modulate the vacuum inlet: open and close the inlet at a first frequency while no sample arrives; and then open and close the inlet at a second frequency while sample arrives; in general, the second frequency is substantially higher than the first frequency. The frequency may be, but not limited, greater then zero to MHz, particularly in tens of KHz, KHz, hundreds of Hz, tens of Hz. (2) only open the vacuum inlet while significant amount of sample arrives, for example, a threshold value could be set in the said first method, signal greater than the threshold will be use to generate the open timing. (3) limit the number of sample to be analyzed under the vacuum conditions.

In one embodiment, a piezoelectric vacuum inlet can be used to control amount of gas and/or sample to be introduced in to the vacuum. A simplified non-limiting example of this instrument is shown in FIG. 1, where a piezoelectric valve 101 is used between an IMS instrument 103 and a MS instrument 105. With the IMS-MS system shown in FIG. 1, a control and data acquisition module located on a computer; Signals communicated to the ion mobility separator 103 control the first gate 104 and second gate 106 of the ion mobility separator, at least a portion of the ions are allowed to enter the ion mobility separator and then allowed to pass through the second gate 106. Drift time (or mobility) of ions are first measured at the ion detector/collector 107. FIG. 1 shows an aperture 111 constructed of a piezoelectric material 112.

The device to restrict the a gas/sample flow does not need to be a piezoelectric valve, any means to control a vacuum inlet size dynamically during analysis of a charged species would be considered useful, such as; magnetic actuator, piezoelectric actuator, mechanical actuator, but not limited to these.

Figure 2:
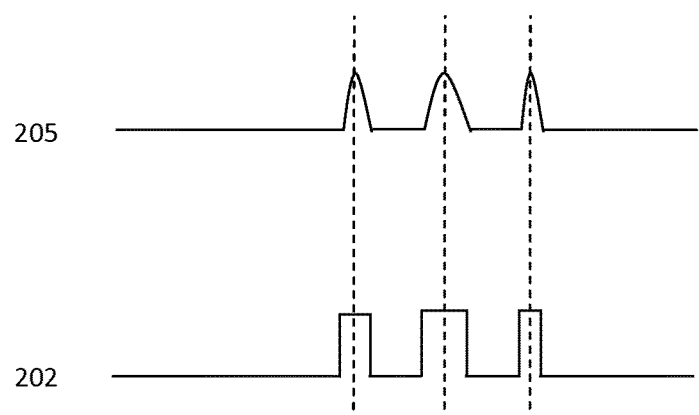
FIG. 2 shows an IMS spectrum obtained outside the vacuum chamber being converted into a timing diagram.

The system could be operated as: (1) IMS survey scan, acquiring single or more spectra; (2) Identifying a peak of interest by the peak's: location, drift time, width, and height to generate a timing diagram for controlling the size of the vacuum inlet. A non-limiting example is shown in FIG. 2. In this example, the open valve timing 202 is the same amount as the peak timing in the IMS spectrum 205 generated by from a detector outside the vacuum inlet.

Figure 3:
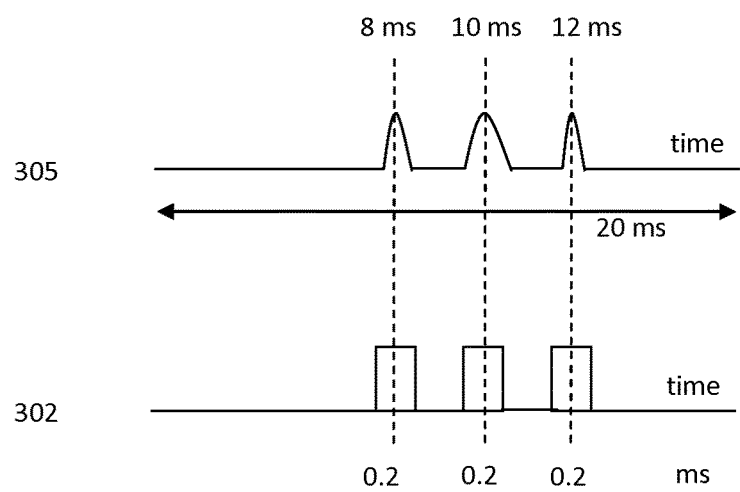
FIG. 3 shows the timing of a switching valve for an IMS spectrum in milliseconds.

An IMS spectrum 305 is taken has a total spectrum length of 20 ms. The detected peak locations are: 8, 10, 12 ms, with a peak width of 0.2 ms. A timing program (diagram) 302 can be processed to look like FIG. 3, such that the vacuum inlet can be opened at 8, 10, 12 ms for a window width at least 0.2 ms. In this non-limiting case, the vacuum inlet only needs to be open (0.2×3/20=0.03) 3% of the time. Therefore, in average only 3% of the pumping load is required for this non-limiting example.

Figure 4:
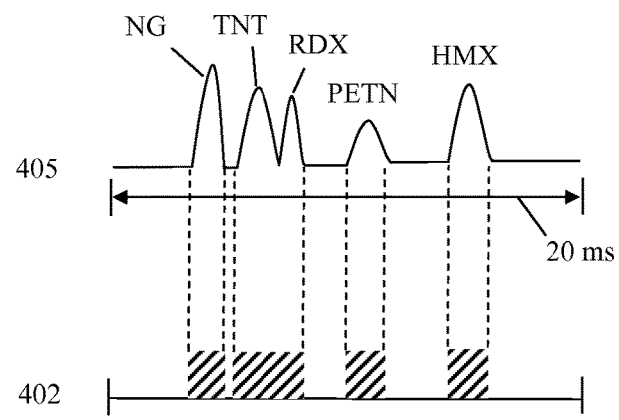
FIG. 4 shows valve timings for targeted explosive chemicals in an IMS spectrum.

A non-limiting specific example of targeted chemicals to be detected is shown in FIG. 4. Drift times in milliseconds for the targeted chemicals are: NG=5.5, TNT=6, RDX=6.5, PETN=8.5, and HMX=9.5 in the IMS spectrum 405. The vacuum inlet will open at the indicated shaded timing areas in the timing diagram 402. The opening timing is not based on the survey scan and is therefore controlled dynamically. The opening timing is preset according to the instrument application purpose. For CWA detection, the opening timing can be completely different from this non-limiting specific example.

Another non-limiting example is under a situation where rapid open and closing of the inlet is required. Under this situation, many ion mobility peaks need to be sampled in a vacuum, the piezoelectric valve may not be able opened/closed fast enough depending on how close are the adjacent peaks (arrival time) of the sample components in a ion mobility based separation. In this case a wider window may be used to cover several peaks, i.e. open vacuum for a longer period of time. The duration of the open/closed valve is based on IMS data obtained outside the vacuum chamber. An example of this situation is shown in FIG. 4 for the TNT and RDX peaks, where the timing program 402 has a wider opening widow for both peaks to enter the inlet. It is worth noting: when the timing program is used to adjust the operational parameters for a mass spectrometer, the mass spectrometer can be guided either to "park" at the m/z for TNT and then "park" at the m/z for RDX, or scan a m/z range that covers the TNT and RDX ions.

In a variety of embodiments, the above example illustrated the basic operation of a mobility indexed mass analysis (MIMA) method for the IMS-MS system. The MIMA operation method includes, but not limited to, using measured ion mobility of a sample to control the mass spectrometer operation for the combined ion mobility—mass analysis involving, introducing mobility separated sample components to a mass spectrometer, adjusting necessary parameters of mass spectrometer systems and subsystems (e.g. ion guides for focusing or storage, lens, analyzer, detector) to the optimized conditions for the analysis of targeted sample components, analyzing m/z of targeted sample components. The m/z of targeted sample components can be predicted based the mass-mobility correlations. Depending on the IMS-MS system configuration and purpose, analyzing ion masses (m/z) may include, but is not limited to, (1) setting the mass spectrometer to analyze one or more m/z to confirm the ion mobility measurement. The method is generally used in detection of targeted compounds (such as in explosive detection) using a scanning type of mass spectrometer, such as quadrupole, ion trap, triple quadrupole, quadruple—time of flight MS, ion trap—time of flight MS, etc. If the ion mobility spectrometer has already detected a target compound, e.g. nitroglycerine (NG) in a sample (FIG. 4), the mass spectrometer will be adjusted to analyze the m/z that related to the NG in order to confirm the IMS detection. In another example, if the measured ion mobility corresponds to more than one m/z values of the compounds of interest (based on the database of the compounds of interest), then the MIMA method will guide the mass spectrometer to analyze more than one m/z of the ion mobility separated sample peak. (2) setting the mass spectrometer to scan over a mass range that is determined using measured ion mobility based on the mass-mobility correlation. This method is used for general purpose IMS-MS analysis without considering a list of targeted compounds; it could limit the mass range needed to be scanned and potentially improve IMS-MS system duty cycle. In general, in a given drift media, measured ion mobility (especially under low field conditions) is directly correlated to the ion mass (m/z), the variation in the mass-mobility correction is related to the structure of the ions. By knowing the possible masses and structures corresponding to an ion mobility value (via either empirical measurements or theoretical calculations), the mass range that needs to be scanned for an ion mobility value can be determined based on this known relationship. Besides the mass range described above, the MIMA method can also be used to control other parameters on the mass spectrometer, these parameter may include, but are not limited to, mass scan rate, mass resolution, mass calibration, DC and/or RF voltages on the analyzer, ion energy, etc.

In one embodiment, with a given pumping power, the amount of time for the inlet to open can be limited. A approach can be taken by opening and closing the inlet at a constant frequency independent from the IMS data or ion mobility peak arrival time. The vacuum inlet can also be run in a modulating mode with a constant frequency. In a non-limiting example, if the opening pulse is narrower than the IMS peak time (width), the IMS-MS can be operated at a reduced pumping load.

The described IMS system can be used to enable portable MS operation and can not only be used to control the MS pumping system (reducing the pumping requirement/load), but also used to cleanup the samples by: (1) using a counter current flow can remove all the neutral chemicals from a dirty sample; (2) only having ions travel to the IMS-MS interface under guidance of the electric field.

In a situation where rapid switching is required, such as having many ion mobility peaks that need to be sampled in a vacuum, the piezoelectric valve may not be opened-closed fast enough. An intelligently placed duration of open-closed timing, can be based on IMS data outside the vacuum chamber, wherein a wider window may be used to cover several peaks, i.e. open vacuum for a longer period of time.

Figure 5:
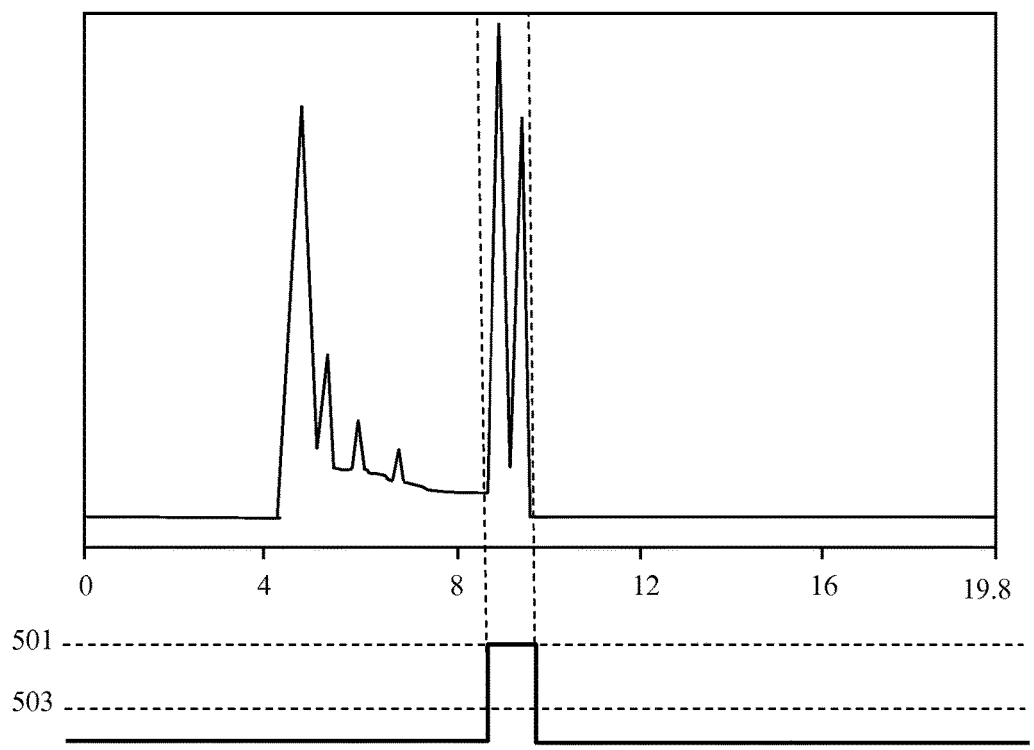
FIG. 5 shows valve opening timing for the ion mobility spectrum of TNT and RDX.

With a given pumping power, the amount of time for the inlet to open can be limited, so several approaches can be taken: (1) Open and close at a high frequency independent from IMS data or ion mobility peak arrival time. The vacuum pump can have a fixed load. The frequency should be higher (the IMS peak width narrower); (2) Open only when ion mobility peaks arrive. In FIG. 5, if an IMS spectrum (either a survey scan or on-the-fly IMS spectrum is used to guide the valve) indicates ions only arrive from 4.5 to 9.8 ms, then the vacuum window can be open from 4.5-9.8 ms for 5.3 ms and closed at the other times. If the total sampling time is 19.8 ms, the (5.3/19.8)=26.8% time for opening of the inlet could reduce the total pumping power by this factor. Assuming the vacuum pump load is not significant over 5.3 ms period to overload it's pumping capacity. In many cases, the ion mobility (timing) of the targeted compound is known, then the vacuum inlet only needs to open for a very short period allowing the targeted molecules to enter. In FIG. 5, assuming the targeted compounds have a drift time from 8.6 to 9.8 ms, a timing program can be used to adjust the inlet structure to open 501 state at 8.6 ms and to close state at 9.8 ms. The vacuum inlet is opened for 1.2 ms, i.e. (1.2/19.8)=6% time opening during the operation. (3) The valve is guided by the IMS signal obtained outside the vacuum chamber, or from the MS detector inside the vacuum chamber. When the survey scan data is used, a measuring is taken and an IMS spectrum is obtained. Then, depending on the signal intensity and timing location, the vacuum valve could be programmed to open for a period of time when ions arrive. Depending on the control mechanism of the vacuum inlet, the control can be done in real time if the valve can open and close fast enough. In this case, the IMS spectrum obtained outside the vacuum chamber is used to generate a timing diagram of valve open-close timing. Depending on time (t) after detection outside vacuum, the requirement of valve operating speed can vary.

Figure 6:
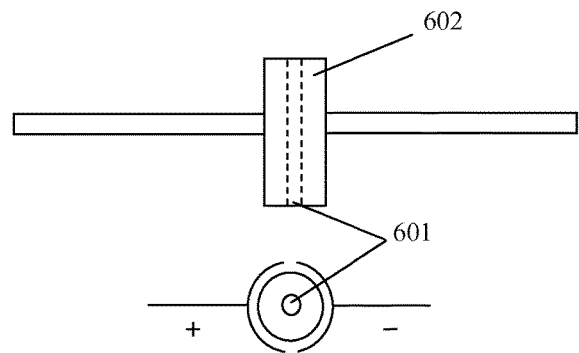
FIG. 6 shows an aperture constructed of a piezoelectric material.

An embodiment of the invention is the material and method to control the opening-closing of the valve. This is an electronically actuated dynamic gas aperture. The aperture can be changed in inner diameter by the application of an electric current. FIG. 6 shows an aperture 601 constructed of a piezoelectric material 602.

Figure 7:
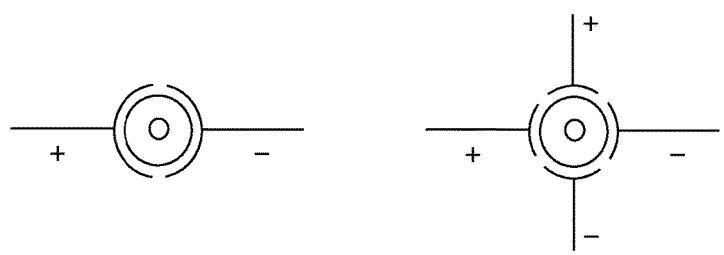
FIG. 7 shows 2 and 4 segmented metalized electrodes.
Figure 8:
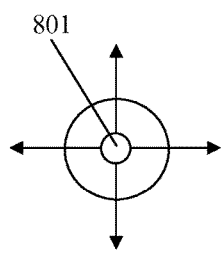
FIG. 8 shows the directions that the aperture may increase.

The body has metalized electrodes to facilitate the creation of an electric field that causes the piezoelectric aperture body to expand and therefore expand the diameter of the aperture. There can be 2, or 4 shown in FIG. 7, or a plurality of segmented metalized electrodes. Upon application of the electric field the bulk body of the tube expands and thereby the aperture ID 801 increases shown in FIG. 8.

Figure 9:
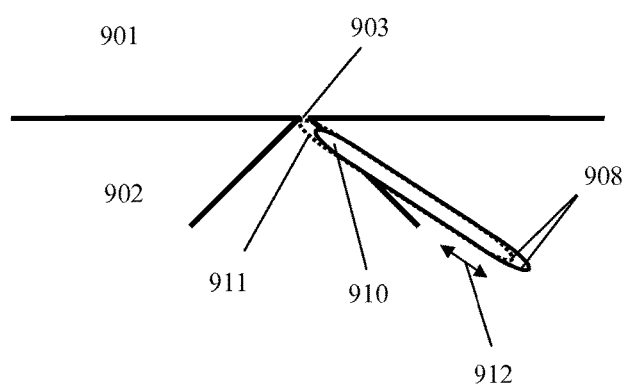
FIG. 9 shows an alternative embodiment of the vacuum inlet that can be controlled by a mechanical arm.

FIG. 9 shows an alternative embodiment of the vacuum inlet 903 that can be controlled by a mechanical arm that is directed connected a fast moving driving component. The driving component could be a piece of piezoelectric material. A non-limiting configuration of piezoelectric controlled vacuum inlet has a mechanical arm 908 that has a surface on one end that can seal against the vacuum inlet body at closed inlet position and is connected the piezoelectric material on the other end. The piezoelectric material controls the movement along the moving direction 912 to open 910 and close 911 the inlet. The vacuum inlet could be a pinhole, capillary or other narrow opening configurations that separates an ambient pressure chamber 901 from a vacuum chamber 902. One end of the arm could be polished to form a vacuum seal against the inlet body. An alternative configuration is to position the arm outside the vacuum chamber; similar movement could be achieved using similar control mechanism.

Figure 12:
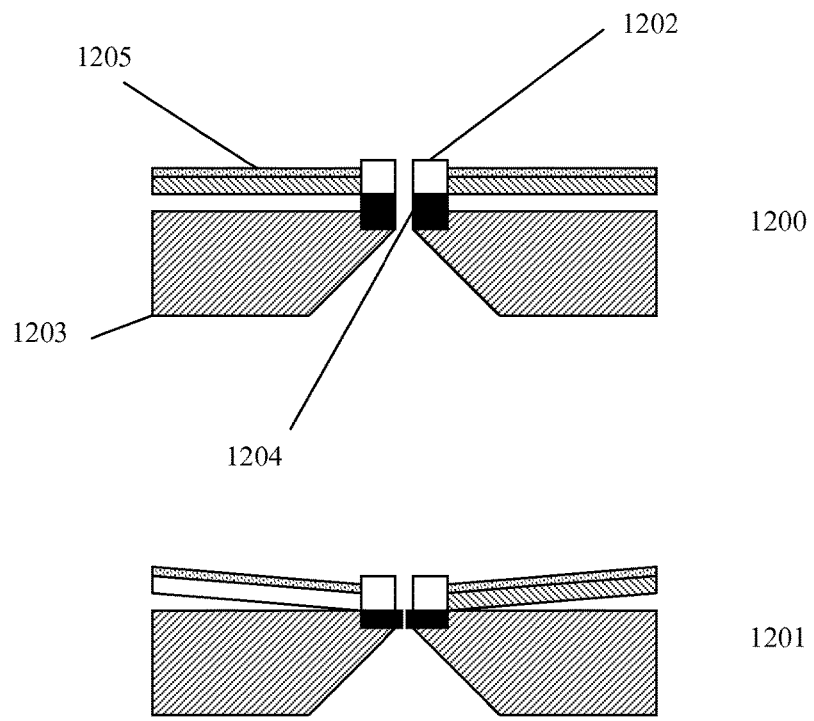
FIG. 12 shows a pulsed inlet using a deformed elastomer.

FIG. 12 shows an alternative embodiment of a pulsed inlet that can be controlled by using a deforming, compressing and/or expanding, elastomer. A piezoelectric disk actuator 1205 controls the opening and closing of the inlet by compressing the elastomer structure (a ring) 1204 with the actuator center ring 1202. The elastomer can be made conductive. The conductive elastomer ring 1204 is set into a retaining depression in the vacuum inlet flange body 1203. The inlet is shown open 1200 and closed 1201.

Figure 13:
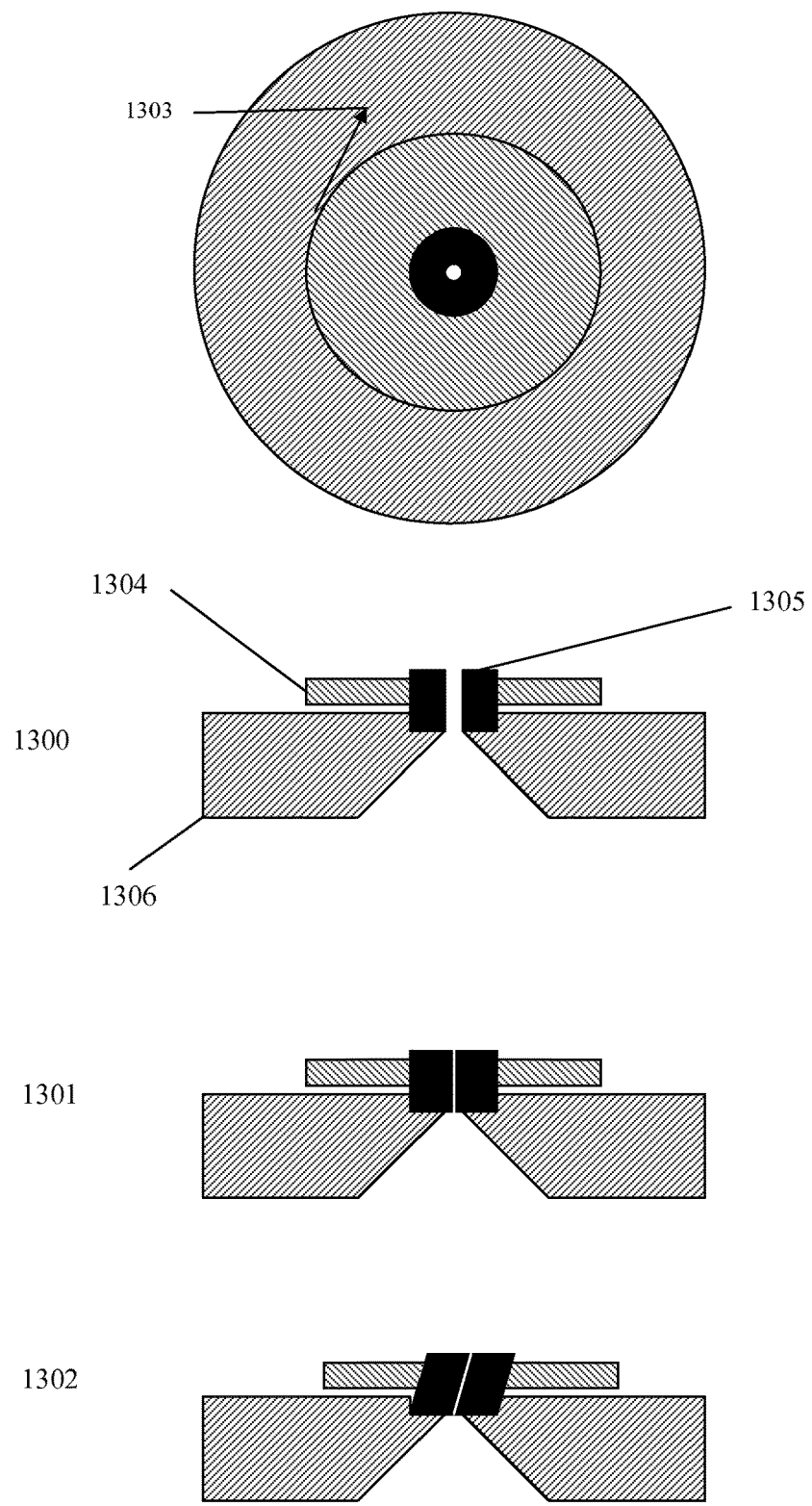
FIG. 13 shows a pulsed inlet using a torsion seal.

FIG. 13 shows an alternative embodiment of the pulsed inlet using a torsion seal. A rotating and/or translating disk 1304 rotates or translates 1303 to close the conductive elastomer inlet 1305. The inlet can be open 1300, rotationally closed 1301, or translationally closed 1302. The conductive elastomer inlet 1305 is set into a retaining depression in the vacuum inlet flange body 1306.

Figure 10A:
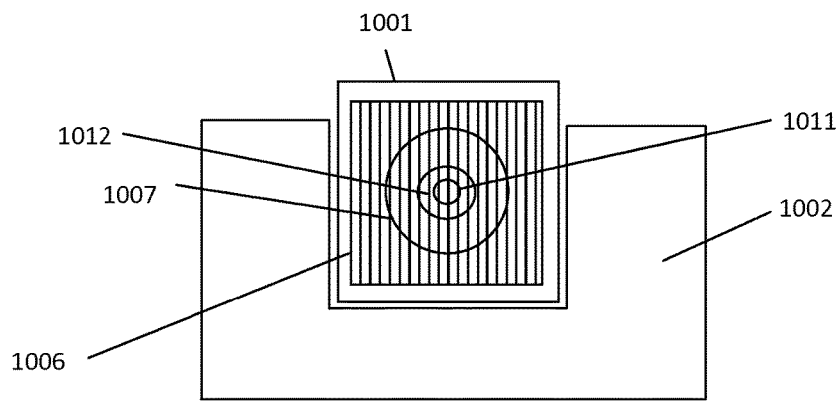
FIG. 10A-B shows a configuration of a portable IMS-MS system; 10A is the front view and 10B is the top view.
Figure 10B:
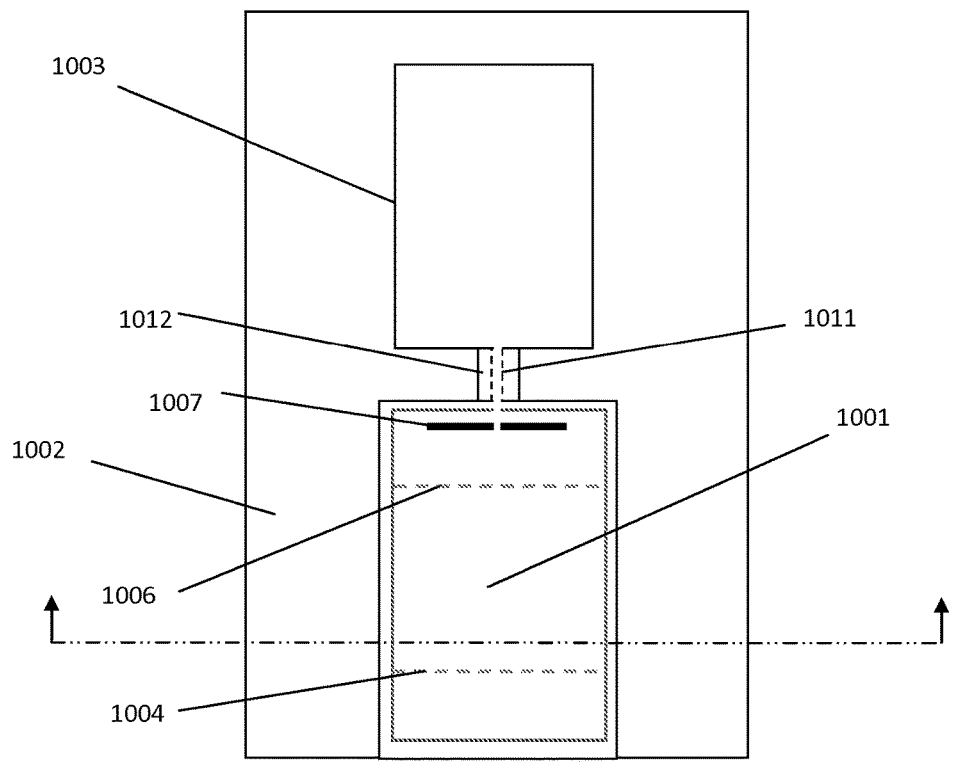

For configuration of a portable IMS-MS system, the size of vacuum chamber should be maximized, thus the vacuum chamber could be constructed as the body the instrument. FIG. 10A-B shows a non-limiting example of the configuration, where the IMS device 1001 is surrounded by vacuum chamber 1002 to achieve maximum size and protection layer of the sensitive instrument. FIG. 10B shows the top view whereby the mass analyzer 1003 is seen. In addition, gas trapping materials with a high surface area, such as molecular sieves and/or zeolites, can also be used to absorb gases temporarily in order to maintain the operating vacuum condition for the mass spectrometer. Such materials could be placed in the routes of the flow path, pumping lines, and/or adjacent to other pressure sensitivity components in the vacuum chamber. With the IMS-MS system shown in FIG. 10B, a control and data acquisition module located on a computer; Signals communicated to the ion mobility separator 1001 control the first gate 1004 and second gate 1006 of the ion mobility separator, at least a portion of the ions are allowed to enter the ion mobility separator and then allowed to pass through the second gate 1006. Drift time (or mobility) of ions are first measured at the ion detector/collector 1007. FIG. 10B shows an aperture 1011 constructed of a piezoelectric material 1012.

Unless otherwise specified in this document the term "vacuum inlet" is intended to mean an interface with the pressure are different on both sides, e.g. one said is substantially ambient pressure and the other side is substantially below ambient pressure; or one side is at a reduced pressure, e.g. 10 torrs, and the other side is at even lower pressure, e.g. millitorrs. In many embodiments illustrated in this invent, the vacuum inlet is used while transporting sample (ions) from relative high pressure to low pressure, however, the same vacuum inlet can also be used to transport samples from low pressure to high pressure. A non-limiting example would be transporting ions from a mass spectrometer to an IMS or flow tube.

Unless otherwise specified in this document the term "ambient pressure" is intended to mean a pressure that is substantially close to atmospheric pressure; the measurement is analysis of the physical and/or chemical properties, which may include analyze samples on the flight or by collecting samples and analyze off-line.

Figure 11:
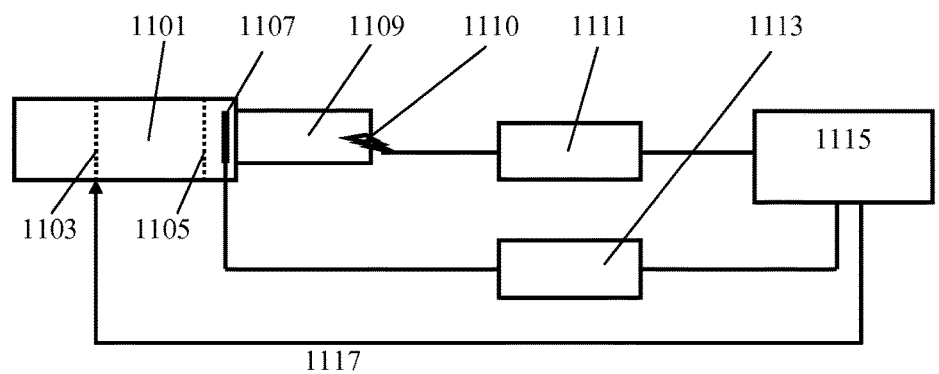
FIG. 11 shows the parts used to measure the mobility outside the vacuum chamber.

For IMS-MS analysis, ion mobility is preferably measured outside the vacuum chamber (under uniform pressure conditions) for better mobility resolution and increased accuracy. FIG. 11 schematically illustrates using measured mobility outside the vacuum chamber to, for example, correct mobility measured inside the vacuum chamber with a MS. With common MS design, additional drift time is added to the mobility measurement when using MS as a detector; ions have traveled through a pressure gradient in the IMS-MS interface and low vacuum ion optics where additional collision occurs. With the IMS-MS system shown in FIG. 11, a control and data acquisition module located on a computer 1115; Signals 1117 communicated to the ion mobility separator 1101 control the first gate 1103 and second gate 1105 of the ion mobility separator, at least a portion of the ions are allowed to enter the ion mobility separator and then allowed to pass through the second gate 1105. Drift time (or mobility) of ions are first measured at the ion detector/collector 1107; the measured ion signal is processed with preamp 1113 and the data acquisition modules on the computer 1115; after a portion of the ions travel through the IMS-MS interface, and then are mass separated in MS 1109 and detected on the MS ion detector 1110. The measured ion signal is then processed with preamp 1111 and the data acquisition modules. Ion mobility spectra generated at ion detectors 1107 and 1110 are processed by the data acquisition module and mobility correction can be made for each individual ion based on their mobility measured outside the vacuum chamber. In various embodiments, a software module can be used to realize such correction/calibration. This procedure is preferred when using an ion collector/detector outside the vacuum chamber for sample collection and MS for ion monitoring and identification. The example of a data acquisition scheme for an IMS-MS systems shown above can be used for ion collection. Ion Gate 1 and Gate 2 are designed to select an ion of interest and to deposit such on the sample collector, or to direct into a mass spectrometer for further analysis or both. Ion mobility spectrometer and mass spectrometer data can be generated through two separate channels and correlated in the data acquisition software.

In various embodiments, the ion detector 1107 used to measure ion mobility outside the vacuum chamber, could also be used as an ion collector that collects at least a portion of the samples for further analysis or other use. In various operational modes of the IMS-MS device, selected ions may be allowed to pass the second ion gate 1105. As a large portion of the selected ions are collected on the ion collector 1107, a small portion of the selected ions may be detected by the MS to identify their mobilities and mass to charge ratio. Similarly, when an field asymmetric ion mobility spectrometer is used as an ion mobility separator, selected ions are allowed to pass through the IMS and detected either on the ion detection/collection plates or a MS located in the vicinity of the detection plates, the rest of the ions are collected at different location of the full profile ion collection plate. In various embodiments, the instrument operating parameters, e.g. compensation voltage and RF frequency, may be used to correlate the location of ions collected on the full profile ion collection plate and ions detected by the MS or ion detection plates.

If the drift time measured outside the vacuum chamber is $t_{out}$ and the m/z data is acquired at $t_{ms}$, then the measured m/z data can be correlated to the mobility data by the factor of a delay time in the interface for each individual ions.

The method for operating an ion mobility separator and a mass spectrometer may include: (a) measuring ion mobility of an analyte component using an ion detector/collector at the end of the ion mobility separator; (b) measuring ion mobility and mass to charge ratio using an ion detector of mass spectrometer; (c) correlating the ion mobility data obtained from mass spectrometer with the ion mobility data from the ion mobility separator. The ions collected on the ion collector at the end of the IMS are mass identified using the correlated ion mobility data.

The IMS-MS instrument of the present inventions can be operated, in various embodiments, as a combined preparative or analytical chiral separation and sample recovery system. For example, with segmented or un-segment Faraday collection plates mounted in the front of MS, a majority of the sample separated by the IMS can be collected on the Faraday plate(s) under high pressure conditions and a small portion of the mobility separated sample can be transported through an interface to the MS. The collection plate can have an opening that matches the geometry of the IMS-MS interface design. The MS can be used as an online monitoring device for what is collected on the collection plate. Selective collection on this plate can be achieved by using asymmetric IMS as an ion filter, by adding a second ion gate for a symmetric IMS, or both. For example, ions with one mobility property (to the best resolution of a given device) are collected on a plate, and used for preparative, analytical purposes, or both. Furthermore, if a transverse electric field at the interface for MS is used; multiple stage ion mobility based separation can be achieved according to ions symmetric or asymmetric ion mobility properties. In various embodiments, this tandem ion mobility separation can produce high mobility separation efficiency.

In various embodiments, a method for operating an instrument comprising: conducting a first measurement using a first instrument; generating a timing program based on the sample arrival time determined by the first measurement; adjusting a vacuum inlet configuration using the timing program; and conducting a second measurement using a second instrument. In on embodiment, the first instrument is an ion mobility spectrometer and the second instrument is a mass spectrometer. Alternatively, the first and second instrument can be any analytical instruments that are compatible and can be used as hyphenated instrument. The first instrument and the second instrument can be the same. The timing program generated using the first measurement can be obtained either on-the-fly or offline during method development time.

In various embodiments, a apparatus of an instrument comprising: a first instrument that is used to conduct a first measurement; using the first measurement result that reflects the sample arrival time to generate a timing program; a vacuum inlet is open and/or closed based on the timing program, and a second instrument operated under vacuum conditions is used to conduct a second measurement, where the first and second instrument can be either ion mobility spectrometer or mass spectrometer.

In various embodiments, a method for operating an instrument comprising: conducting an first measurement using a first method; generating an timing program based on the sample arrival time determined by the first measurement; adjusting operational parameters of a second method using the timing program; and conducting an second measurement using the second method.

What is claimed is:

1. A method for operating a hyphenated ion mobility spectrometer—mass spectrometer comprising:
   a. ionizing a sample to produce an ion beam containing sample ions;
   b. separating the sample ions based on ion mobility to create an ion mobility separated ion beam;
   c. splitting the ion mobility separated ion beam such that an ion detector of the ion mobility spectrometer receives a first continuous uninterrupted portion of the ion beam, and an inlet of the mass spectrometer receives a second continuous uninterrupted portion of the ion beam;
   d. measuring a first signal from the first portion of the ion beam using the ion detector of the ion mobility spectrometer;
   e. measuring a second signal from the second portion of the ion beam using the mass spectrometer.

2. The method in claim 1, wherein the ion detector of the ion mobility spectrometer is either at the ambient pressure or vacuum pressure.

3. The method in claim 1, wherein the ion detector of the ion mobility spectrometer is outside a vacuum inlet of the mass spectrometer.

4. The method in claim 1, wherein the first signal and the second signal are measured simultaneously.

5. The method in claim 1, wherein the first signal of ion mobility measurement and the second signal of mass measurement are correlated.

6. A hyphenated ion mobility spectrometer mass—spectrometer instrument comprising:
   a. an ion source that ionizes a sample to produce an ion beam containing sample ions;
   b. an ion mobility spectrometer that separates the sample ions based on ion mobility to create an ion mobility separated ion beam;
   c. a first detector that measures a first signal from a first continuous uninterrupted portion of the ion mobility separated ion beam while at the same time allowing a second continuous uninterrupted portion of the ion mobility separated ion beam into an inlet of a mass spectrometer.

7. The instrument in claim 6, wherein the first detector is either at the ambient pressure or vacuum pressure.

8. The instrument in claim 6, wherein the first detector is outside a vacuum inlet of the mass spectrometer.

9. The method of claim 1, wherein the ion detector of the ion mobility spectrometer is a Faraday plate.

10. The method of claim 9, where the Faraday plate has a hole that allows a portion of the ion beam to pass through the Faraday plate.

11. The instrument of claim 6, wherein the ion detector of the ion mobility spectrometer is a Faraday plate.

12. The instrument of claim 11, where the Faraday plate has a hole that allows a portion of the ion beam to pass through the Faraday plate.

* * * * *